United States Patent [19]

Sheldon et al.

[11] 4,110,362

[45] Aug. 29, 1978

[54] PREPARATION OF ESTERS

[75] Inventors: Roger A. Sheldon; Peter Been, both of Amsterdam, Netherlands

[73] Assignee: Shell Oil Company, Houston, Tex.

[21] Appl. No.: 765,186

[22] Filed: Feb. 3, 1977

[30] Foreign Application Priority Data

Mar. 1, 1976 [GB] United Kingdom ............... 8045/76
Mar. 1, 1976 [GB] United Kingdom ............... 8046/76

[51] Int. Cl.$^2$ ................ C07C 120/00; C07C 121/66
[52] U.S. Cl. .................................................. 260/465 D
[58] Field of Search ................................... 260/465 D

[56] References Cited

U.S. PATENT DOCUMENTS 3,835,176  9/1974  Matsuo et al. ............... 260/465 D

OTHER PUBLICATIONS

Zymalkowski et al., *Arch. pharmaz Ber. pharmaz. Ges.*, 62, Nr. 5, pp. 218–224, (1956).
Francis et al., *J. Chem. Soc.*, 95, pp. 1403–1409, (1909).
Kinder et al., *Arch. Pharm.*, 271, pp. 431–439, (1933).
Coronyn, *J. Org. Chem.*, 14, pp. 1013–1022, (1949).
Fisher et al., *J. Org. Chem.*, 24, pp. 1650–1654, (1959).

*Primary Examiner*—Dolph H. Torrence

[57] ABSTRACT

Certain carboxylic acid esters also containing a cyano group are prepared by reacting an acid halide, an aldehyde and a water-soluble cyanide in the presence of a water-immiscible aprotic solvent and an onium catalyst.

31 Claims, No Drawings

PREPARATION OF ESTERS

BACKGROUND OF THE INVENTION

1. Field of the Invention

The invention relates to a process for the preparation of certain cyano-substituted-carboxylic acid esters by reacting an acid halide, an aldehyde and a water-soluble cyanide.

2. Description of the Prior Art

According to U.S. Pat. No. 3,835,176, addition of substituted cyclopropanecarbonyl halides and m-substituted benzaldehydes, if necessary dissolved in an aprotic solvent, to an aqueous solution of sodium cyanide or potassium cyanide and stirring of the mixture obtained until no more conversion takes place, affords the desired esters. The experiment described in Example 4 of the above U.S. patent was conducted in the absence of a solvent, with an unsaturated aqueous solution of sodium cyanide, with a 20% molar excess of the cyclopropanecarbonyl halide (calculated on aldehyde) and at a temperature of 0° C.

Such a process has the disadvantages that the yield of the ester is relatively low and that keeping the temperature at 0° C and using the said molar excess are expensive.

The present invention obviates these disadvantages.

SUMMARY OF THE INVENTION

The present invention is directed to a process for the preparation of an ester of formula I

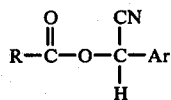

wherein Ar is an optionally substituted aromatic group and R is an optionally substituted acyclic or saturated cyclic hydrocarbyl group, by contacting an aromatic aldehyde of the formula ArC(O)H and an acyl halide of the formula RC(O)Hal, in which formulas Ar and R have the same meanings as in formula I and Hal is a halogen atom having an atomic number of from 9 to 53, inclusive, with water, a water-soluble cyanide, a substantially water-immiscible aprotic solvent and an onium phase transfer catalyst.

The onium catalyst can be (1) a quaternary onium compound of the formula

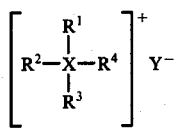

wherein X is a nitrogen, phosphorus or arsenic atom, $R^1$, $R^2$, $R^3$ and $R^4$ each independently is an alkyl group of 1 to 20 carbon atoms, an aralkyl or alkaryl group of 7 to 9 carbon atoms or an aryl group of 6 to 12 carbon atoms and Y is a monovalent ion; or (2) a sulfonium compound of the formula

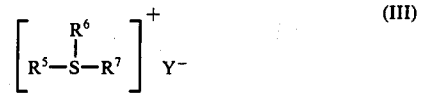

wherein $R^5$, $R^6$ and $R^7$ each independently is an alkyl group of 1 to 40 carbon atoms and Y is a monovalent ion.

In formulas II and III above, Y can be hydroxide, halide, (alkyl)sulfate, (alkyl)sulfonate, (aryl)sulfonate, tetrafluoroborate, phosphate, nitrate or alkyl- or arylcarboxylate. For example, Y can be chloride, bromide, iodide, methylsulfate, tosylate, acetate, formate, citrate, tartrate, benzoate or the like.

Examples of suitable onium compounds are tetra-n-butylammonium bromide, tetra-n-butylammonium chloride, methyltri-2-methylphenylammonium chloride, tetramethylphosphonium iodide, tetra-n-butylphosphonium bromide, methyltriphenylarsonium iodide, ethyl-2-methylpentadecyl-2-methylundecylsulfonium ethylsulfate, methyldinonylsulfonium methylsulfate and n-hexadecyldimethylsulfonium iodide. Further suitable onium compounds are described in U.S. Pat. No. 3,917,667 and allowed U.S. Ser. Nos. 587,783 and 587,574. Very good results have been obtained with quaternary ammonium compounds.

The onium compound may be a hydroxide or salt and is used as the functional portion of a strongly basic anion exchange resin having a structural portion (polymer matrix) and a functional portion (ion-active group). Of special importance are polystyrene resins, such as copolymers of aromatic monovinyl compounds and aromatic polyvinyl compounds, particularly styrene/divinylbenzene copolymers. The functional portion is a quaternary ammonium, phosphonium or arsonium group. Examples of strongly basic anion exchange resins which may be employed are those derived from trimethylamine (such as the products known under the trade names of "Amberlite IRA-400", "Amberlite IRA-401", "Amberlite IRA-402", "Amberlite IRA-900", "Duolite A-101-D", "Duolite ES-111", "Dowex 1", "Dowex 11", "Dowex 21K" and "Ionac A-450" (all ten trade names are registered trade marks) and those derived from dimethylethanolamine (such as the products known under the trade names of "Amberlite IRA-410", "Amberlite IRA-911", "Dowex 2", "Duolite A-102-D", "Ionac A-542" and "Ionax A-550" (all six trade names are registered trademarks). Very good results have been obtained with those derived from trimethylamine. When these catalysts are available in a neutralized form, for instance in the chloride form, they must be activated to the hydroxyl form by treatment with an aqueous alkali metal hydroxide, for example sodium hydroxide, and washed with water to remove salt anions before use.

More particularly, one preferred subclass of catalysts of formula II are those in which $R^1$, $R^2$, $R^3$ and $R^4$ each independently is an alkyl group of 1 to about 8 carbon atoms such as methyl-trioctylammonium chloride, tributylammonium bromide, tetra-n-butylammonium hydroxide, bromide or chloride, methyl-tri-2-methylheptylammonium chloride, tetramethylammonium bromide, tetrabutylphosphonium bromide or tetraethylammonium bromide. Other suitable catalyst of this type are known under the trade names "Hyamine 1622", "Hyamine 2389", "Hyamine 3500", "Aliquat 336" and "Adogen 464" (all five trade names are registered trade marks).

Another preferred subclass of catalysts of formula II are those containing one or more phenyl or benzyl groups as $R^1$, $R^2$, $R^3$ and $R^4$ such as benzyltriethylammonium chloride or ethyltriphenylphosphonium bromide or the like.

Examples of catalysts of formula III are triethylsulfonium iodide, di-sec-decyl-methylsulfonium chloride, n-hexadecyldimethylsulfonium methyl sulfate, sec-dodecyl-sec-hexadecylethylsulfonium ethyl sulfate, sec-hexadecyldimethylsulfonium iodide, sec-hexadecylmethylethylsulfonium tosylate, sec-hexadecyldimethylsulfonium tosylate, trimethylsulfonium bromide and di-n-butylmethylsulfonium iodide. Preferred catalysts of formula III are those in which $R^5$, $R^6$ and $R^7$ each independently is an alkyl group of 3 to 16 carbon atoms. The preparation of catalysts of formula III is described in U.S. Pat. No. 3,917,667.

The molar ratio of the amount of phase transfer catalyst to the amount of aromatic aldehyde of the formula ArC(O)H may vary within wide limits, but is suitably from 1:5 to 1:500. The use of low molar ratios will require a longer time to complete the reaction, whilst the use of higher molar ratios naturally increases the cost to produce a given quantity of ester. Thus, the choice of reaction time and molar ratio catalyst to aromatic aldehyde are mutually interdependant, and in any individual instance will depend on the local economic factors. Very good results are usually obtained at molar ratios from 1:10 to 1:100.

Another advantage of the process according to the present invention is that the molar ratio of the amount of (cyclo)aliphatic acyl halide to the amount of aromatic aldehyde can be kept so low that a molar excess of the halide is not or hardly not required. This molar ratio is preferably in the range of from 1.1 to 1.0. When the substantially water-immiscible aprotic solvent is a (cyclo)alkane or a mixture of (cyclo)alkanes molar ratios equal to 1.0 give excellent results.

The molar ratio of the amount of water-soluble cyanide to the amount of aromatic aldehyde is suitably from 1.5 to 1.00 and preferably from 1.3 to 1.02. By "water-soluble cyanide" is meant a water-soluble salt of hydrogen cyanide. Of the water soluble cyanides alkali-metal cyanides and alkaline-earth-metal cyanides are preferred. Sodium cyanide is particularly preferred, because it affords the esters of the formula I in the shortest reaction time.

The temperature at which the process is conducted is suitably above 0° C and is preferably in the range of from 10° to 50° C. Very good results have been obtained at temperatures in the range of from 15° to 40° C. The process has the advantage that ambient temperatures are very suitable.

Suitable substantially-water-immiscible aprotic solvents are aromatic hydrocarbons and chlorinated hydrocarbons, for example benzene, toluene, o-, m- and p-xylene, the trimethylbenzenes, dichloromethane, 1,2-dichloromethane, chloroform, monochlorobenzene and 1,2- and 1,3-dichlorobenzene. Very good results have been obtained with toluene.

Among the many aprotic solvents alkanes and cycloalkanes favor the shortest reaction times. Moreover, the esters of the formula I are thus obtained in a very high yield. Examples of suitable alkanes and cycloalkanes are those having up to 10 carbon atoms, preferably 6 to 10 carbon atoms, e.g., n-hexane, n-heptane, n-octane, n-nonane, n-decane and their isomers, (for example 2-methylpentane, 3-methylpentane, 2-methylhexane, 3-methylhexane and 2,4,4-trimethylpentane) and cyclohexane and methylcyclohexane. N-heptane and cyclohexane are very suitable solvents. Gasolines rich in alkanes are also very suitable, for example those with a boiling range at atmospheric pressure between 40° and 65° C, 60° and 80° C, or 80° and 110° C. The cyclo(alkanes) used according to the invention may contain up to 50% by weight of other substantially water-immiscible aprotic solvents, for example aromatic hydrocarbons or chlorinated hydrocarbons.

The process according to the present invention may be conducted starting from unsaturated or saturated aqueous solutions of water-soluble cyanide and in the latter case in the presence or absence of solid-water-soluble cyanide. The use of solid water-soluble cyanide is covered in our concurrently filed U.S. patent application Ser. No. 765,184, filed Feb. 3, 1977.

It has been found that when in a given case in which in successive comparable experiments less water and more solid water-soluble cyanide are applied (starting from a saturated aqueous solution of cyanide containing no solid water-soluble cyanide and keeping the total amount of water-soluble cyanide constant) the reaction time can be kept shorter and shorter, passes a minimum and then becomes longer and longer until it has become as long as in the starting case.

The use of (cyclo)alkanes in combination with aqueous solutions of cyanide in the absence of solid water-soluble cyanide allows very short reaction times. The use of aromatic hydrocarbons or chlorinated hydrocarbons in combination with aqueous solutions of cyanide in the absence of solid water-soluble cyanide needs longer reaction times, but the use of these two groups of solvents in combination with solid water-soluble cyanide allows very short reaction times. Solid water-soluble cyanide may also be used in the presence of (cyclo)alkanes, but the reaction times can already be kept very short in the absence of the former. The above-mentioned minimum reaction time is usually obtained when molar ratios of the amount of water to the total amount of water-soluble cyanide is higher than 0.05 and particularly in the range of from 0.05 to 1. For comparison it may be stated that the molar ratios of water to sodium cyanide in a saturated aqueous solution of sodium cyanide at 10° and 35° C are 5.7 and 3.3, respectively. Consequently, extremely small amounts of water are sufficient to obtain the shortest reaction times. Furthermore, the yield of the ester of the formula I is usually very high and sometimes quantitative. In addition to the possibility of using short reaction times the use of solid water-soluble cyanide has a cost-saving effect, since smaller volumes of water can be handled.

Other examples of substantially water-immiscible aprotic solvents are dialkyl ethers and substantially water-immiscible alkanones each containing from 4 to about 8 carbon atoms for example diethyl ether, diisopropyl ether and diisobutyl ketone. For these solvents the above-mentioned minimum reaction time can easily be determined by means of simple experiments in which the molar ratio of the amount of water to the total amount of water-soluble cyanide is varied. Mixtures of solvents, for example of n-heptane containing up to 10% by weight of benzene and/or toluene.

The optionally substituted aromatic group Ar in the aromatic aldehyde of the formula ArC(O)H may be carbocyclic or heterocyclic. Examples of carbocyclic groups are phenyl, 1-naphthyl, 2-naphthyl and 2-anthryl groups. Heterocyclic aromatic groups are derived from hetero-aromatic compounds which are defined as in Kirk-Othmer, "Encyclopedia of Chemical Technology", Second Edition, Volume 2 (1963), page 702; obtained by replacement of one or more carbon atoms of a carbocyclic aromatic compound by a hetero-atom—for example pyridine, pyrimidine, pyrazine, quinoline and isoquinoline—and also include those heterocyclic compounds having five-membered rings which show aromatic characteristics and are mentioned on page 703 of said volume, for example thiophene, pyrrole, furan, indole and benzothiophene. As an aromatic group an optionally substituted phenyl group is very suitable. Examples of substituents are hydrocarbyl and hydrocarbyloxy groups. Very good results have been obtained with phenoxybenzaldehydes, particularly m-phenoxybenzaldehyde.

The group R in the formula RC(O)Hal may, for example, be an optionally substituted alkyl group. The alkyl group may be straight or branched. The alkyl groups preferably have a tertiary or quaternary carbon atom bound to the group —C(O)Hal. Examples of such alkanoyl halides are 2-methylpropanoyl chloride, 2,2-dimethylpropanoyl chloride and 2-methylbutanoyl bromide. Very good results have been obtained with 2-methylpropanoyl chloride. The alkyl group may carry as substituents, for example, hydrocarbyloxy or substituted phenyl groups, such as halophenyl or alkylphenyl. Very good results have been obtained with 1-(4-chlorophenyl)-2-methylpropyl groups. The expression "saturated cyclic hydrocarbyl group" in this patent application refers to cyclic hydrocarbyl groups in which the ring is saturated; this ring may carry substituents for example, alkyl groups of 1 to 6 carbon atoms, such as methyl, halogen atoms having atomic numbers of 9 to 35, inclusive, such as chlorine, bromine or fluorine, or unsaturated side chains, such as isobutenyl, dichlorovinyl or dibromovinyl. Examples of saturated cyclic hydrocarbyl groups are cyclopropyl, cyclobutyl and cyclohexyl groups. Very good results have been obtained with optionally substituted cyclopropanecarbonyl halides, particularly with 2,2,3,3-tetramethylcyclopropanecarbonyl halides and 2-(2,2-dichlorovinyl)-3,3-dimethylcyclopropanecarbonyl halides. The latter halides may have a cis or trans structure or may be a mixture of such structures and may be a pure optical isomer or a mixture of optical isomers.

The atom Hal in the formula RC(O)Hal is preferably a chlorine or bromine atom and in particular a chlorine atom.

The process according to the invention may be carried out by gradual addition of the acyl halide to a vigorously agitated, e.g., stirred, mixture of the other starting compounds (particularly recommended when R in the formula RC(O)Hal represents a 2,2,3,3-tetramethylcyclopropyl group) and often by placing together the total amounts of the starting compounds and vigorous agitating, e.g., stirring, of the mixture thus formed, which is particularly recommended when R represents a 1-(4-chlorophenyl)-2-methylpropyl, an isopropyl or a 2-(2,2-dichlorovinyl)-3,3-dimethylcyclopropyl group.

The process is of particular interest to prepare pesticidally active esters, for example: when the aromatic aldehyde is 3-phenoxybenzaldehyde and the acyl halide is an aralkyl halide such as 2-(4-chlorophenyl)-3-methylbutanoyl chloride, or a substituted-cyclopropanecarbonyl halide such as 2,2,3,3-tetramethylcyclopropanecarbonyl chloride or 2-(2,2-dichlorovinyl)-3,3-dimethylcyclopropanecarbonyl chloride, because the esters then formed are α-cyano-3-phenoxybenzyl 2-(4-chlorophenyl)-3-methylbutanoate, α-cyano-3-phenoxybenzyl 2,2,3,3-tetramethylcyclopropanecarboxylate and α-cyano-3-phenoxybenzyl 2-(2,2-dichlorovinyl)-3,3-dimethylcyclopropanecarboxylate, respectively, all of which are pesticidally active compounds as in Belgian patent 801,946, U.S. Pat. No. 3,835,176 and Netherlands publication No. 7,307,130, respectively.

EXAMPLES

The Examples further illustrate the invention. All experiments were conducted at a temperature of 23° C. The sodium cyanide used consisted of particles having a largest dimension of 0.5 mm and contained 0.44% by weight of water. The molar ratio of water to sodium cyanide has been calculated taking into accound the water present in the sodium cyanide and the water added, if any. For comparison it may be stated that the molar ratio of water to sodium cyanide in a saturated aqueous solution of sodium cyanide having a temperature of 23° C is 4.1. The reaction mixtures were stirred virorously and analysed by gas-liquid chromatography to determine the yield of the ester formed. Reaction mixtures were filtered to remove precipitated sodium chloride and solid sodium cyanide, if any, and drying of solutions was carried out over anhydrous sodium sulphate. Flashing of the solvent took place in a film evaporator at a pressure of 15 mm Hg. All yields are calculated on starting aromatic aldehyde.

EXAMPLE I

Preparation of α-cyano-3-phenoxybenzyl 2-(4-chlorophenyl)-3-methylbutanoate in the presence of n-heptane A 50 ml round-bottomed flask equipped with a magnetic stirrer was charged with 10 mmol of 3-phenoxybenzaldehyde, 10 mmol of 2-(4-chlorophenyl)-3-methylbutanoyl chloride, 12 mmol of sodium cyanide, water, a catalyst, if any, and 20 ml of n-heptane and the mixture thus formed was stirred. Six experiments were carried out in this manner, see Table I.

Table I

| 1 | 2 | 3 | 4 | 5 | 6 |
|---|---|---|---|---|---|
| | Catalyst | | | Reaction | Yield |
| Exp. no. | name | amount %mol on aldehyde | Water added ml | time h | of ester, % |
| 1[1)] | — | — | 1.0 | 3 | 86 |
| | | | | 18 | more than 99 |
| 2 | methyl-tri-2-methyl-heptylammonium chloride | 5 | 1.0 | 2 | 96 |
| | | | | 4 | 99 |
| 3 | tetra-n-butyl-ammonium chloride | 2 | 1.0 | 1 | 80 |
| | | | | 4 | 99 |
| 3 | " | 2 | 2.0 | 1 | 50 |
| | | | | 5 | 99 |
| 5 | tetra-n-butylphosphonium bromide | 2 | 1.0 | 1 | 74 |
| | | | | 3 | 99 |
| 6 | n-hexadecyldimethylsulfonium iodide | 2 | 1.0 | 1 | 66 |
| | | | | 3 | 97 |

[1)]not according to the invention.

Column 1 in Table I states the number of the experiment, column 2 the catalyst, column 4 the amount of water added to the starting mixture (excluding the water present in the sodium cyanide) and column 5 the reaction time. In none of the experiments solid NaCN was present. The yield of the desired ester is presented in column 6. The sodium cyanide was completely dissolved.

EXAMPLE II

Preparation of α-cyano-3-phenoxybenzyl 2-(2,2-dichlorovinyl)3,3-dimethylcyclopropanecarboxylate in the presence of n-heptane A 50 ml round-bottomed flask equipped with a magnetic stirrer was charged with 10 mmol of 3-phenoxybenzaldehyde, an amount of 2-(2,2-dichlorovinyl)-3,3-dimethylcyclopropanecarbonyl chloride, 12 mmol of sodium cyanide, water, a catalyst, if any and 20 ml of n-heptane. The mixture thus formed was stirred. Seven experiements were carried out in this manner, see Table II. Column 3, 4 and 5 state the amounts of catalyst, water and acyl chloride added. The sodium cyanide was completely dissolved. The yield of the desired ester is presented in column 7.

of 10.5 mmol of 2-(4-chlorophenyl)-3-methylbutanoyl chloride was used.

TABLE III

| 1 | 2 | 3 | 4 | 5 | 6 |
|---|---|---|---|---|---|
| Exp. no. | Catalyst | Water added, ml | Molar ratio water to NaCN | Reaction time, h | Yield of ester, % |
| 1[1] | none | — | 0.012[2] | 3 | 19 |
|  |  |  |  | 20 | 18 |
| 2 | tetra-n-butylammonium bromide | — | 0.012[2] | 2 | 30 |
|  |  |  |  | 22 | 32 |
| 3[1] | none | 0.02 | 0.105[2] | 3 | 38 |
|  |  |  |  | 24 | 98 |
|  |  |  |  | 44 | 99 |
| 4 | tetra-n-butylammonium bromide | 0.02 | 0.105[2] | 2 | 81 |
|  |  |  |  | 18 | 98 |
| 5[1] | none | 1.00 | 4.64 | 3 | 41 |
|  |  |  |  | 24 | 87 |
|  |  |  |  | 85 | 95 |
| 6 | tetra-n-butylammonium bromide | 1.00 | 4.64 | 2 | 71 |
|  |  |  |  | 22 | 81 |
|  |  |  |  | 44 | 86 |

[1] not according to the invention.
[2] solid NaCN was present.

Table II

| 1 | 2 | 3 | 4 | 5 | 6 | 7 |
|---|---|---|---|---|---|---|
|  | Catalyst | | | | | |
| Exp. no. | %mol on name | amount added aldehyde | Water ml | Acyl chloride, mmol | Reaction time, h | Yield of ester, % |
| 1[1] | — | — | 1.0 | 10.2 | 3 | 49 |
|  |  |  |  |  | 21 | 94 |
|  |  |  |  |  | 44 | 99 |
| 2 | methyl-tri-2-methyl-heptylammonium chloride | 5 | 1.0 | 10.2 | 1 | 96 |
|  |  |  |  |  | 2 | 96.5 |
| 3 | " | 2 | 1.0 | 10.5 | 1 | 95 |
|  |  |  |  |  | 3 | more than 99 |
| 4 | " | 0.2 | 1.0 | 10.5 | 1 | 48 |
|  |  |  |  |  | 17 | 99 |
| 5 | " | 2 | 2.0 | 10.5 | 1 | 90 |
|  |  |  |  |  | 5 | 94 |
|  |  |  |  |  | 22 | 96 |
| 6 | tetra-n-butylammonium chloride | 2 | 1.0 | 10.5 | 1 | 90 |
|  |  |  |  |  | 4 | 99 |
| 7 | Amberlite IRA 400[2] | (1 gram) | 1.0 | 10.5 | 1 | 54 |
|  |  |  |  |  | 5 | 95 |

[1] not according to the invention
[2] a registered trade name for a strongly basic anion exchange resin having a styrene/divinylbenzene copolymer as polymer matrix and a quaternary ammonium group as ion-active group. The chloride form was used.

EXAMPLE III

Preparation of α-cyano-3-phenoxybenzyl 2-(4-chlorophenyl)-3-methylbutanoate in the presence of toluene A 50 ml roundbottomed flask equipped with a magnetic stirrer was charged with 10 mmol of 3-phenoxybenzaldehyde, 10.5 mmol of 2-(4-chlorophenyl)-3-methylbutanoyl chloride, 12 mmol of sodium cyanide and 20 ml of toluene. The mixture thus formed was stirred. The yields of the desired ester after 3 and 20 hours' stirring are presented in Table III, see experiment 1.

Five other experiments were conducted in this manner, see Table III. Columns 2 and 3 in Table III state the catalyst and amount of water if any, respectively, added to the starting mixture, and column 4 states the molar ratio of water to sodium cyanide. The amount of catalyst added was 2%m in the experiments 2, 4 and 6 and 10% m, calculated on 3-phenoxybenzaldehyde, in experiments 7 and 11. In experiment 11, 10.0 mmol instead

EXAMPLE 4

Preparation of α-cyano-3-phenoxybenzyl 2-(4-chlorophenyl)-3-methylbutanoate in the presence of dichloromethane A 50 ml round-bottomed flask equiped with a magnetic stirrer was charged with 10.0 mmol of 3-phenoxybenzaldehyde, 10.5 mmol of 2-(4-chlorophenyl)-3-methylbutanoyl chloride, 12 mmol of sodium cyanide, 0.02 ml of water and 20 ml of dichloromethane. The mixture thus formed was stirred. The yield of the desired ester is stated in Table IV, experiment 1.

TABLE IV

| Exp. no. | Catalyst | Water added, ml | Molar ratio water to NaCN | Reaction time, h | Yield of ester, % |
|---|---|---|---|---|---|
| 1[1] | none | 0.02 | 0.105[2] | 2 | 34 |
|  |  |  |  | 18 | 46 |
| 2 | tetra-n-butylammonium bromide | 0.02 | 0.105[2] | 2 | 54 |
|  |  |  |  | 18 | 84 |

TABLE IV-continued

| Exp. no. | Catalyst | Water added, ml | Molar ratio water to NaCN | Reaction time, h | Yield of ester, % |
|---|---|---|---|---|---|
| | | | | 40 | 96 |
| 3 | " | 1.00 | 4.64 | 3 | 65 |
| | | | | 6 | 74 |
| | | | | 70 | 87 |

[1] not according to the invention.
[2] solid NaCN was present.

Experiments 2 and 3 are repetitions of experiment 1, the differences being that tetra-n-butylammonium bromide was used in an amount of 2%m, calculated on 3-phenoxybenzaldehyde and that the amounts of water stated in Table IV, column 3, were added.

EXAMPLE 5

Preparation of α-cyano-3-phenoxybenzyl 2,2,3,3-tetramethylcyclopropanecarboxylate in the presence of n-heptane.

Methods A and B were applied to prepare the ester wanted.

Method A

A 50 ml round-bottomed flask equipped with a magnetic stirrer was charged with 10 mmol of 3-phenoxybenzaldehyde, 10 mmol of 2,2,3,3-tetramethylcyclopropanecarbonyl chloride, 12 mmol of sodium cyanide, 1.00 ml of water, a catalyst, if any, and 20 ml of n-heptane. The molar ratio of water to NaCN was 4.64, solid NaCN being absent. The catalyst was added in an amount of 0.20 mmol. The mixture thus formed was stirred for 1.5 hours and analysed.

Method B

The flask used for method A was charged with 10 mmol of 3-phenoxybenzaldehyde, 12 mmol of sodium cyanide, 10 ml of n-heptane, 1.00 ml of water and 0.20 mmol of a catalyst, if any, the molar ratio of water to mmol of NaCN being 4.64. An amount of 10 mmol of 2,2,3,3-tetramethylcyclopropanecarbonyl chloride dissolved in 10 ml of n-heptane was introduced into the flask during a period of 70-75 min. The yield of the ester was determined at the end of this period.

Three experiments were carried out in this manner. Table V states the catalysts used, if any. This Table also presents the yield of the desired ester.

TABLE V

| Exp. no. | Catalyst | Yield of ester, % Method A | Yield of ester, % Method B |
|---|---|---|---|
| 1* | none | 17 | 40 |
| 2 | tetra-n-butylammonium chloride | 20 | 98 |
| 3 | methyl-tri-2-methylheptyl-ammonium chloride | 18 | 96 |

*[1] not according to the invention

The amounts of the catalysts used were 2%m in the experiments 2 and 3, calculated on 3-phenoxybenzaldehyde.

The reaction mixture obtained in experiment 3, method B, was filtered and the filtrate washed twice with 20 ml of a 1 M aqueous solution of sodium bicarbonate and once with 20 ml of water. The washed filtrate was dried and the n-heptane was flashed from the dried filtrate to obtain the ester as a pale yellow oil. This oil was dissolved in 2.5 ml of methanol at 23° C and the solution obtained was cooled to a temperature of −20° C to give a precipitate of the ester. The ester was filtered and had a purity of more than 98%.

EXAMPLE 6

Preparation of α-cyano-3-phenoxybenzyl 2-(4-chlorophenyl)-3-methylbutanoate on an enlarged scale Methods A (not according to the invention), B and C were compared for the preparation of the ester wanted.

Method A, in the absence of a phase transfer catalyst.

A 500 ml round-bottomed flask equipped with a paddle stirrer was charged with 100 mmol of 3-phenoxybenzaldehyde, 100 mmol of 2-(4-chlorophenyl)-3-methylbutanoyl chloride, 120 mmol of sodium cyanide, 10 ml of water (which dissolved all sodium cyanide) and 200 ml of n-heptane. After stirring for 45 hours the mixture was warmed to a temperature between 40° and 50° C and filtered. The filtrate was washed twice with 50 ml of 1 M aqueous sodium bicarbonate solution, once with 50 ml of water, dried and the n-heptane was flashed from the dried solution to give the desired ester in a yield of 99% and a purity of 96%.

Method B, in the presence of an onium compound.

The experiment described in section A of this Example was repeated in the presence of 2%m of tetra-n-butylammonium chloride, calculated on 3-phenoxybenzaldehyde. After two hours the ester was obtained in a yield of 99% with a purity of 94%.

What is claimed is:

1. A process for the preparation of an ester of formula I $$R-\overset{O}{\underset{\|}{C}}-O-\overset{CN}{\underset{\underset{H}{|}}{C}}-Ar \qquad (I)$$

wherein Ar represents a phenoxy substituted phenyl group and R is an alkyl group optionally substituted by halophenyl or alkylphenyl or a cyclopropyl group optionally substituted by alkyl, halogen, isobutenyl, dichlorovinyl or dibromovinyl, which process comprises contacting an aromatic aldehyde of the formula ArC(O)H and a (cyclo)aliphatic acyl halide of the general formula RC(O)Hal, in which formulas Ar and R have the same meaning as in formula I and Hal represents a halogen atom having an atomic number of from 9 to 53, inclusive, with water, a water-soluble cyanide, a substantially water-immiscible aprotic solvent and a quaternary onium phase transfer catalyst of the formula II $$\left[\begin{array}{c} R^1 \\ | \\ R^2-X-R^4 \\ | \\ R^3 \end{array}\right]^+ Y^- \qquad (II)$$

wherein X represents a nitrogen, phosphorus or arsenic atom, $R^1$, $R^2$, $R^3$ and $R^4$ each an alkyl, aralkyl, alkaryl or aryl group and Y a monovalent ion, or a sulfonium compound of the formula III

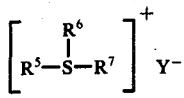

wherein $R^5$, $R^6$ and $R^7$ each represents an alkyl group and Y a monovalent ion and recovering the desired ester product from the reaction mixture.

2. A process according to claim 1, in which the molar ratio of the amount of phase transfer catalyst to the amount of aromatic aldehyde of the formula ArC(O)H is from 1:5 to 1:500.

3. A process according to claim 1, which is conducted at a temperature in the range of from 10° to 50° C.

4. A process according to claim 1, in which the total amount of the water-soluble cyanide is dissolved in the water.

5. A process according to claim 4, in which the substantially water-immiscible aprotic solvent is a (cyclo)alkane or a mixture of (cyclo)alkanes.

6. A process according to claim 5, in which the alkane is n-heptane.

7. A process according to claim 5, in which the cycloalkane is cyclohexane.

8. A process according to claim 1, which is conducted in the presence of solid water-soluble cyanide.

9. A process according to claim 8, in which the substantially water-immiscible aprotic solvent is an aromatic hydrocarbon or a mixture of aromatic hydrocarbons.

10. A process according to claim 9, in which the aromatic hydrocarbon is toluene.

11. A process according to claim 8, in which the substantially water-immiscible aprotic solvent is a chlorinated hydrocarbon.

12. A process according to claim 8, in which the starting molar ratio of the amount of water to the total amount of water-soluble cyanide is higher than 0.05.

13. A process according to claim 12, in which the starting molar ratio of the amount of water to the total amount of water-soluble cyanide is in the range of from 0.05 to 1.

14. A process according to claim 1, in which the molar ratio of the amount of (cyclo)aliphatic acyl halide of the formula RC(O)Hal to the amount of the aromatic aldehyde of the formula ArC(O)H is in the range of from 1.1 to 1.0.

15. A process according to claim 14, in which the molar ratio of the amount of (cyclo)aliphatic acyl halide of the formula RC(O)Hal to the amount of the aromatic aldehyde of the formula ArC(O)H is 1.0.

16. A process according to claim 1, in which the water-soluble cyanide is sodium cyanide.

17. A process according to claim 1, in which Hal in the formula RC(O)Hal represents a chlorine atom.

18. A process according to claim 1, in which the group R in the formula RC(O)Hal is an optionally substituted (cyclo)alkyl group having a tertiary or quaternary carbon atom bound to the group —C(O)Hal.

19. A process according to claim 18, in which the group R is a 1-(4-chlorophenyl)-2-methylpropyl group.

20. A process according to claim 18, in which the group R is an isopropyl group.

21. A process according to claim 18, in which the group R is an optionally substituted cyclopropyl group.

22. A process according to claim 21, in which the group R is a 2,2,3,3-tetramethylcyclopropyl group.

23. A process according to claim 21, in which the group R is a 2-(2,2-dichlorovinyl)-3,3-dimethylcyclopropyl group.

24. A process according to claim 19, which is carried out by forming a mixture of the total amounts of the aromatic aldehyde, the (cyclo)aliphatic acyl halide, the water, the water-soluble cyanide and the substantially water-immiscible aprotic solvent, and stirring the mixture thus formed.

25. A process according to claim 22, which is carried out by gradual addition of the cycloaliphatic acyl halide to a stirred mixture of the aromatic aldehyde, the water, the water-soluble cyanide and the substantially water-immiscible aprotic solvent.

26. A process according to claim 1 wherein the catalyst is a quaternary ammonium compound of formula II in which $R^1$, $R^2$, $R^3$ and $R^4$ each independently is an alkyl group containing 1 to 20 carbon atoms, an aralkyl or alkaryl group containing 7 to 9 carbon atoms or an aryl group containing 6 to 12 carbon atoms.

27. A process according to claim 26 wherein the water soluble cyanide is sodium cyanide.

28. A process according to claim 27 wherein the solvent is an alkane, a cycloalkane, an aromatic hydrocarbon, chlorinated hydrocarbon or a mixture thereof.

29. A process according to claim 28 which is conducted at a temperature in the range of from 10° to 50° C, with the molar ratio of the amount of (cyclo)aliphatic acyl halide to the amount of the aromatic aldehyde from 1.1 to 1.0 and in which the starting molar ratio of the amount of water to the total amount of water-soluble cyanide is higher than 0.05.

30. A process according to claim 29 wherein the ammonium catalyst of formula II is one in which $R^1$, $R^2$, $R^3$ and $R^4$ each independently is an alkyl group containing from 1 to 8 carbon atoms, phenyl or benzyl.

31. A process according to claim 30 wherein the ester of formula I is α-cyano-3-phenoxybenzyl 2-(-4-chlorophenyl)-3-methylbutanoate.

* * * * *